US009579463B2

(12) United States Patent
Okihara

(10) Patent No.: US 9,579,463 B2
(45) Date of Patent: Feb. 28, 2017

(54) BARREL FOR SYRINGE AND PRE-FILLED SYRINGE

(71) Applicant: Terumo Kabushiki Kaisha, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/061,643

(22) Filed: Mar. 4, 2016

(65) Prior Publication Data

US 2016/0184529 A1 Jun. 30, 2016

Related U.S. Application Data

(63) Continuation of application No. PCT/JP2014/073176, filed on Sep. 3, 2014.

(30) Foreign Application Priority Data

Sep. 6, 2013 (JP) ................................ 2013-185526

(51) Int. Cl.
*A61M 5/32* (2006.01)
*A61M 5/31* (2006.01)
*A61M 5/28* (2006.01)
*A61M 5/315* (2006.01)

(52) U.S. Cl.
CPC ............ *A61M 5/3134* (2013.01); *A61M 5/28* (2013.01); *A61M 5/31505* (2013.01); *A61M 2005/3104* (2013.01); *A61M 2005/3106* (2013.01)

(58) Field of Classification Search
CPC ................ A61M 5/002; A61M 5/3202; A61M 2005/3104; A61M 5/50
USPC ................................. 604/199, 192–198, 110
See application file for complete search history.

(56) References Cited

U.S. PATENT DOCUMENTS

| | | | | |
|---|---|---|---|---|
| 5,413,563 A | 5/1995 | Basile et al. | | |
| 2012/0184920 A1* | 7/2012 | Okihara | A61M 5/1452 | 604/222 |

FOREIGN PATENT DOCUMENTS

| | | |
|---|---|---|
| JP | H09-512727 A | 12/1997 |
| JP | H11-501597 A | 2/1999 |
| JP | 4156791 B2 | 9/2008 |
| WO | WO-96/25964 A1 | 8/1996 |
| WO | WO-2011/040522 A1 | 4/2011 |
| WO | WO-2013/048863 A1 | 4/2013 |

OTHER PUBLICATIONS

International Search Report for PCT/JP2014/073176 mailed Dec. 9, 2014.

* cited by examiner

*Primary Examiner* — Phillip Gray
(74) *Attorney, Agent, or Firm* — Foley & Lardner LLP

(57) ABSTRACT

A syringe barrel includes an barrel main body having a cylinder tip at a distal end of the barrel main body; and a cap detachably attached to the cylinder tip by threaded engagement to seal an opening of the cylinder tip. The cylinder tip comprises at least one projection that projects radially from an outer periphery of a proximal end part of the cylinder tip. The cap includes a cylindrical cover that covers an outer periphery of the cylinder tip. A proximal-side inner periphery of the cover comprises a reduced radius portion, and, when the cap is threadedly engaged with the cylinder tip, a distance from a rotation axis of the cap to the reduced radius portion is smaller than a distance from the rotation axis to an outer end of the at least one projection.

10 Claims, 13 Drawing Sheets

BARREL FOR SYRINGE AND PRE-FILLED SYRINGE

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2014/073176, filed on Sep. 3, 2014, which claims priority to Japanese Patent Application No. JP2013-185526, filed on Sep. 6, 2013. The contents of these applications are hereby incorporated by reference in their entireties.

BACKGROUND

The present disclosure relates to a syringe barrel and a pre-filled syringe.

One type of known conventional syringe is a pre-filled syringe that has previously been filled with a liquid drug or the like (see, for example, JP 11-501597 T and Japanese Patent No. 4156791). It is important that the liquid drug or the like contained in the pre-filled syringe is prevented from leaking through a distal end opening of the syringe before its use, particularly during transport. Therefore, a cap is attached to the syringe barrel of the pre-filled syringe to seal the cylinder tip (syringe distal end opening) of the main body of the barrel in a liquid-tight manner.

A known structure for attaching the cap to the cylinder tip is one in which the cap is attached to the cylinder tip only by threaded engagement to seal a nozzle tip in a liquid-tight manner (see, for example, JP 11-501597 T). However, in a case where the cap is attached to the cylinder tip only by threaded engagement, there is a fear that the threaded engagement is loosened by vibration or the like during transport so that leakage of the liquid drug or the like contained in the syringe occurs.

For this reason, a structure for preventing the loosening of the cap is disclosed in which (i) a projection (inward projection) that projects inward from the inner periphery of the cap and (ii) a projection (outward projection) that projects outward from the outer periphery of the cylinder tip to be engaged with the inward projection, are engaged with each other to increase the rotational resistance of the cap against the cylinder tip (see, for example, Japanese Patent No. 4156791).

SUMMARY OF THE INVENTION

However, the cap and the barrel main body shrink in each of molding and sterilization steps, and therefore it is difficult to exactly engage the inward projection and the outward projection with each other at the time when the cap is threadedly engaged with the cylinder tip. In a case where the inward projection and the outward projection are not exactly engaged with each other in a state where the cap is threadedly engaged with the cylinder tip—that is, in a case where the loosening-preventing structure rattles—loosening of the cap is not sufficiently prevented.

In consideration of such a problem, one object of certain embodiments of the present invention to provide a syringe barrel and a pre-filled syringe that can appropriately fulfill the function of preventing the loosening of the cap.

In order to achieve the above object, one embodiment of the present invention is directed to a syringe barrel including: an barrel main body having a cylinder tip at a distal end of the barrel main body; and a cap detachably attached to the cylinder tip by threaded engagement to seal an opening of the cylinder tip, wherein the cylinder tip has a projection formed to radially project from a outer periphery of a proximal end part of the cylinder tip, wherein the cap has a cylindrical cover that covers an outer periphery of the cylinder tip, wherein a proximal-side inner periphery of the cover has a reduced radius portion, and a distance from a rotation axis of the cap to the reduced radius portion at the time when the cap is threadedly engaged with the cylinder tip is smaller than a distance from the rotation axis to an outer end of the projection, and wherein the reduced radius portion of the cover is formed in a production process of the syringe barrel by expanding a part of the proximal-side inner periphery of the cover outward by the projection and thereby deforming other part of the proximal-side inner periphery inward, and is engaged with the projection to prevent loosening of the cap in a state where the cap is attached to the cylinder tip.

In this syringe barrel, the reduced radius portion of the cover that is engaged with the projection to prevent the loosening of the cap is obtained as a result of deformation of the proximal-side inner periphery caused by a force received from the projection, and therefore the projection and the cover establish an accurate positional relationship when engaged with each other. Therefore, it is not necessary to align a threaded engagement structure between the cap and the cylinder tip with the projection, and therefore it is possible to easily obtain a rattle-free structure for preventing the loosening of the cap. Further, the reduced radius portion of the cover that is engaged with the projection is formed in the proximal-side inner periphery of the cover, and therefore engagement between the projection and the cover is released only by slightly rotating the cap. Thus, the cap can be easily opened.

In the above syringe barrel, the proximal-side inner periphery of the cover before production of the syringe barrel may have a circular cross-sectional shape perpendicular to an axis of the cover. In this case, the proximal-side inner periphery of the cover is reliably deformed to have a non-circular cross-sectional shape at the time when the cap is attached (at the completion of threaded engagement), and therefore the reduced radius portion can be reliably formed. Thus, the effect of preventing the loosening of the cap can be reliably obtained.

In the above syringe barrel, the projection may be provided by projecting two projections in opposite directions with respect to an axis of the cylinder tip. In this case, the proximal-side inner periphery of the cover is deformed by the projections provided to be opposed to each other, and has an elliptical cross-sectional shape. Therefore, the reduced radius portions can be more reliably formed, which is highly effective at preventing the loosening of the cap and makes it possible to hold the cap coaxially with the cylinder tip.

In the above syringe barrel, the cap may have a sealing part that is in close contact with a distal end of the cylinder tip and is made of an elastic material, and the sealing part may be pressed by the distal end of the cylinder tip to seal the opening of the cylinder tip in a state where the cap is attached to the cylinder tip. In this case, even when a force is always applied to the cap in a direction in which threaded engagement is loosened due to the elastic force of the sealing part, loosening of the cap is effectively prevented by resistance to cause the reduced radius portion of the cover to overpass the projection.

In the above syringe barrel, an engagement force between the reduced radius portion of the cover and the projection may be larger than a disengagement force exerted on the cap based on an elastic force of the sealing part. This structure makes it possible to reliably prevent the loosening of the cap.

In the above syringe barrel, the reduced radius portion of the cover may be formed by performing heat treatment in a state where the cap is attached to the cylinder tip. In this case, it is possible to easily obtain a structure in which the projection is accurately engaged with the proximal-side inner periphery of the cover.

In the above syringe barrel, the heat treatment may be autoclave sterilization. The autoclave sterilization is performed in the production process of the syringe barrel, and therefore the reduced radius portion in the proximal-side inner periphery of the cover can be efficiently obtained.

In the above syringe barrel, the cylinder tip may be a female luer being configured that a male luer is insertable into and connectable to the female luer.

In the above syringe barrel, the cylinder tip may have a male luer being insertable into and connectable to a female luer, and a cylindrical lock adaptor that surrounding an outer periphery of the male luer and having a female screw formed on a inner periphery of the cylindrical lock adaptor, and the projection may be formed on an outer periphery of the lock adaptor.

Another embodiment of the present invention is directed to a pre-filled syringe including: the above syringe barrel; a gasket that is liquid-tightly and slidably movable in the barrel main body; and a drug filled in a filling chamber defined by the barrel main body, the gasket, and the cap.

The syringe barrel and the pre-filled syringe according to embodiments of the present invention can suitably fulfill the function of preventing the loosening of the cap.

DETAILED DESCRIPTION

Herein below, a syringe barrel and a pre-filled syringe according to embodiments of the present invention will be described with reference to the accompanying drawings.

Figure 1:
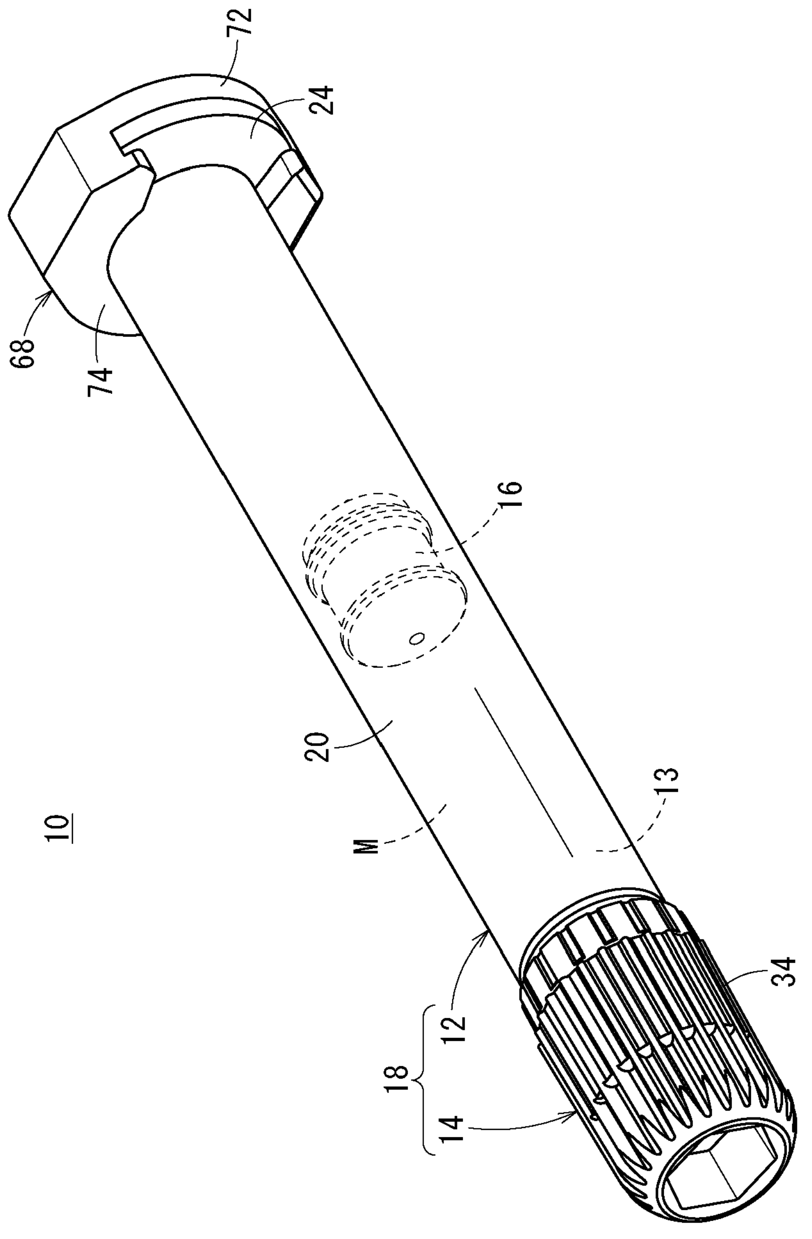
FIG. 1 is a perspective view of a pre-filled syringe according to a first embodiment of the present invention.
Figure 2:
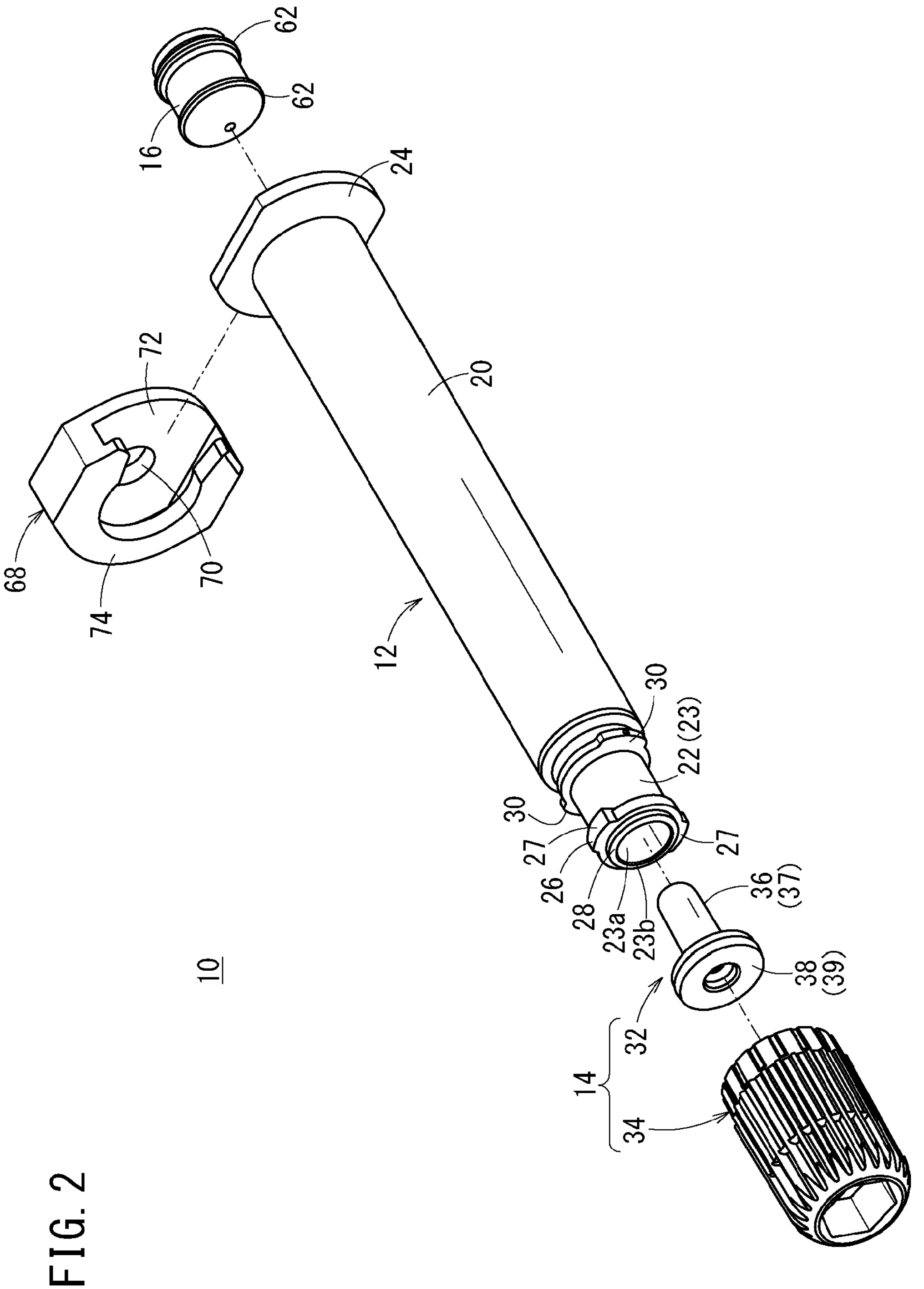
FIG. 2 is an exploded perspective view of the pre-filled syringe shown in FIG. 1.
Figure 3:
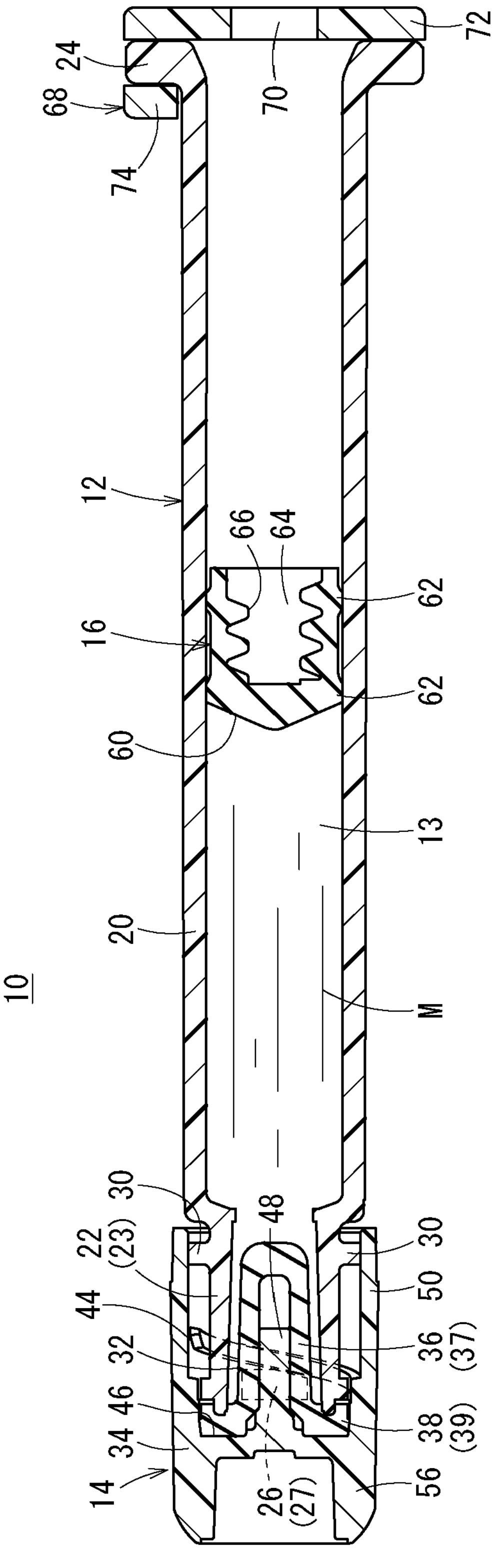
FIG. 3 is a longitudinal sectional view of the pre-filled syringe shown in FIG. 1.
Figure 4:
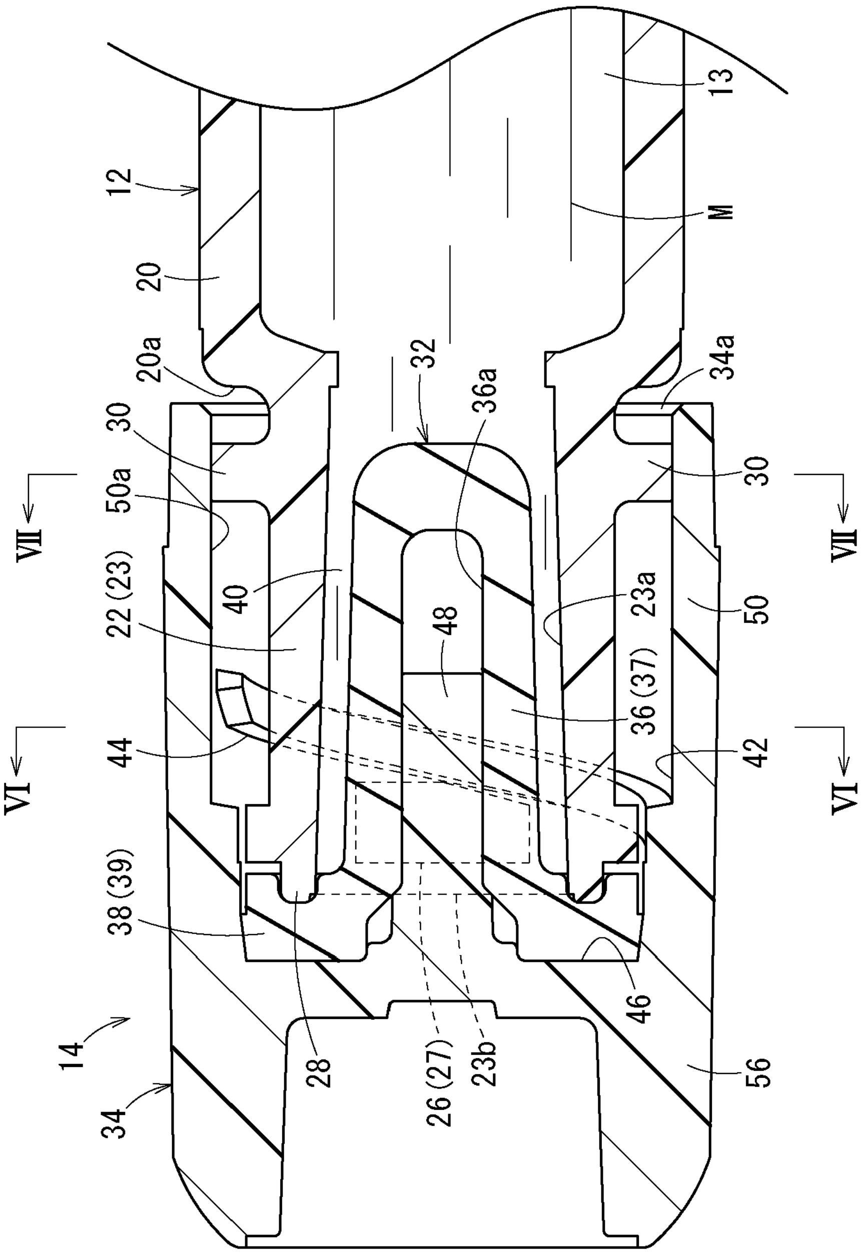
FIG. 4 is a partially-enlarged view of FIG. 3.

FIG. 1 is a perspective view of a pre-filled syringe 10 according to a first embodiment of the present invention. FIG. 2 is an exploded perspective view of the pre-filled syringe 10. FIG. 3 is a longitudinal sectional view of the pre-filled syringe 10. FIG. 4 is an enlarged longitudinal sectional view of the distal end of the pre-filled syringe 10.

The pre-filled syringe 10 includes, as its main components, a cylindrical barrel main body 12 having a cylinder tip 22, a cap 14 that seals the cylinder tip 22 of the barrel main body 12, a gasket 16 that is liquid-tightly and slidably movable in the barrel main body 12, and a drug M filled in a filling chamber 13 formed in the barrel main body 12. In this pre-filled syringe 10, the barrel main body 12 and the cap 14 constitute a syringe barrel 18.

As shown in FIG. 2 and FIG. 3, the barrel main body 12 has a body part 20 constituting the main part of the barrel main body 12, a cylinder tip 22 provided at the distal end of the body part 20, and a flange 24 formed to radially project outward from the proximal end of the body part 20. The cylinder tip 22 projects from the distal end of the barrel main body 12 in the distal direction so as to have a diameter smaller than that of the barrel main body 12. The cylinder tip 22 constitutes a female luer 23 into and to which a male luer 82 can be inserted and connected (see FIG. 8B). The female luer 23 has a tapered inner periphery 23*a* (see FIG. 4) whose inner diameter increases toward the distal direction.

As shown in FIG. 2, on the distal-side outer periphery of the female luer 23, a male screw 26 is provided to detachably fix the cap 14. In this embodiment, the male screw 26 is constituted from two engagement projections 27 that project in opposite directions with respect to the axis of the barrel main body 12. Further, at the distal end of the female luer 23, a ring-shaped pressing part 28 that projects in the distal direction and extends in the circumferential direction around the axis of the barrel main body 12. The pressing part 28 presses a sealing part 39 that will be described later along the entire circumference of an opening 23*b* in a state where the cap 14 is fixed (attached) to the female luer 23.

On the outer periphery of a proximal end part of the female luer 23, a projection 30 is provided to prevent the loosening of the cap 14 before use. In this embodiment, a pair of projections 30 is provided which projects in opposite directions with respect to the axis of the barrel main body 12. In a state where the cap 14 is fixed to the female luer 23, the projections 30 are engaged with a proximal-side inner periphery 50*a* of a cover 50 that will be described later. In this way, the projections 30 prevent the loosening of threaded engagement between the cap 14 and the female luer 23. It is to be noted that the function of the projection 30 to prevent the loosening of the cap 14 will be described again after description of the specific structure of the cap 14. The projections 30 are provided near the proximal end of the female luer 23, that is, provided at a position slightly spaced apart from a distal end surface 20*a* of the body part 20 in the distal direction (see FIG. 4).

Examples of a constituent material of the barrel main body 12 having such a structure as described above include various resins such as polypropylene, polyethylene, polystyrene, polyamide, polycarbonate, polyvinyl chloride, poly-(4-methylpentene-1), acrylic resins, acrylonitrile-butadiene-styrene copolymers, polyesters such as polyethylene terephthalate, and cyclic polyolefins. Among them, resins such as polypropylene and cyclic polyolefins are preferred for ease of molding and heat resistance.

Next, the structure of the cap 14 detachably attached to the female luer 23 will be described. As shown in FIGS. 2 to 4, the cap 14 has an elastic member 32 that seals the opening 23*b* of the female luer 23, and a main body 34 that supports the elastic member 32. In a state where the cap 14 is attached to the female luer 23 before use, the opening 23*b* of the female luer 23 is liquid-tightly sealed with the cap 14 (see FIG. 2) so that the drug M does not leak through the opening 23*b*.

The elastic member 32 is placed in the main body 34 (in a recess 42 that will be described later). The elastic member 32 has a cylindrical part 36 that has an open distal end and a closed proximal end and extends in the axial direction of the cap 14, and a flange part 38 that surrounds the distal opening of the cylindrical part 36 and radially projects outward. The elastic member 32 is formed by integrally molding the cylindrical part 36 and the flange part 38 without gap between them. The cylindrical part 36 constitutes an insertion part 37 inserted into the female luer 23. The flange part 38 constitutes a sealing part 39 that seals the opening 23*b* of the female luer 23.

Examples of a constituent material of the elastic member 32 include: various rubber materials such as natural rubber, butyl rubber, isoprene rubber, butadiene rubber, styrene-butadiene rubber, and silicone rubber; various thermoplastic elastomers such as polyurethane-based thermoplastic elastomers, polyester-based thermoplastic elastomers, polyamide-based thermoplastic elastomers, olefin-based thermoplastic elastomers, and styrene-based thermoplastic elastomers; and mixtures of two or more of them.

As shown in FIG. 4, the insertion part 37 is spaced apart from the inner periphery 23*a* of the female luer 23 in a state where the cap 14 is fixed (attached) to the female luer 23. That is, the outer diameter of the insertion part 37 is smaller than the inner diameter of the female luer 23, and therefore an annular gap 40 is created between the inner periphery 23*a* of the female luer 23 and the outer periphery of the insertion part 37. The annular gap 40 is in communication with the inside of the body part 20 of the barrel main body 12.

Further, in a state where the cap 14 is fixed (attached) to the female luer 23, the sealing part 39 is in close contact with the distal end surface (pressing part 28) of the female luer 23 along the entire circumference of the opening 23*b* of the female luer 23, and is dented in the distal direction by pressing with the pressing part 28 in the distal direction. It is to be noted that the sealing part 39 has a flat proximal end surface in its natural state (in a state where the sealing part 39 is not pressed with the pressing part 28).

The main body 34 of the cap 14 is made of a material harder than the elastic member 32 (e.g., a material mentioned above as an example of the constituent material of the barrel main body 12), and has a recess 42 opened in the proximal direction. Specifically, the main body 34 has a female screw 44 that is threadedly engaged with the male screw 26 provided in the female luer 23, a supporting part 46 that supports the flange part 38 of the elastic member 32, an anti-rotation part 48 that prevents the relative rotation of the elastic member 32 with respect to the main body 34, and a cover 50 that covers the outer periphery of the female luer 23. It is to be noted that the outer periphery of the main body 34 has surface irregularities formed to prevent slipping at the time when the cap 14 is rotated.

The female screw 44 is formed to project from the inner periphery of the cover 50. The supporting part 46 is formed by the outer periphery-side bottom of the recess 42, and the flange part 38 of the elastic member 32 is inserted and held in the supporting part 46. The anti-rotation part 48 projects from the center of the bottom of the recess 42 in the proximal direction along the axis of the cap 14. The free end of the supporting part 46 (the proximal end of the cap 14) is positioned on the distal side of a proximal opening 34*a* of the main body 34.

Figure 5:
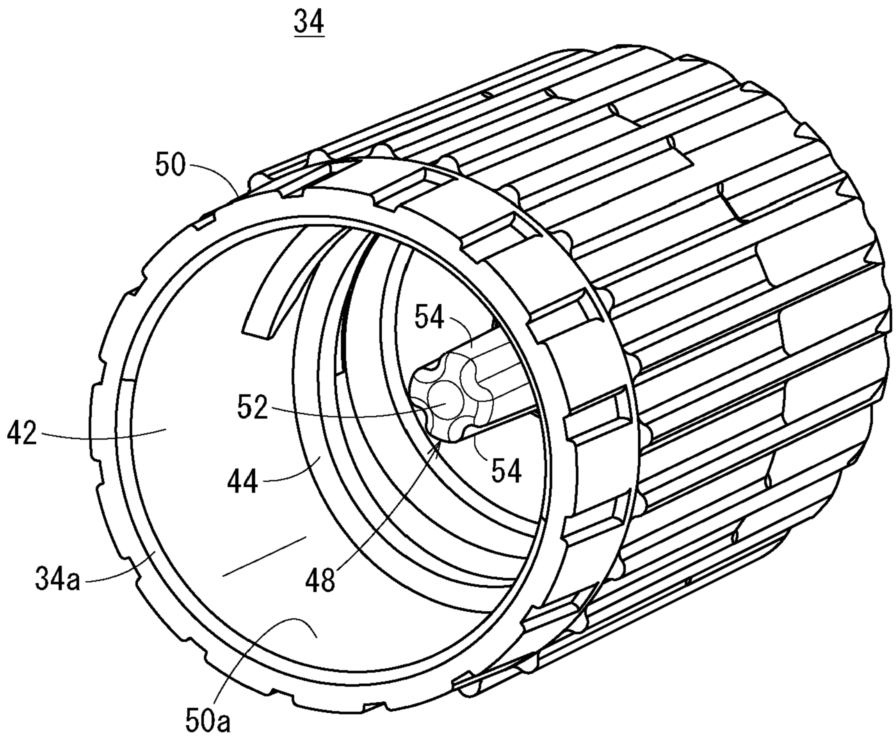
FIG. 5 is a perspective view of a main body of a cap viewed from the proximal end side of the main body.

The anti-rotation part 48 is inserted into the cylindrical part 36 of the elastic member 32 and engaged with an inner periphery 36*a* of the cylindrical part 36. Specifically, as shown in FIG. 5, the anti-rotation part 48 has a columnar part 52 that extends in the axial direction of the cap 14, and a plurality of ribs 54 that project outward from the outer periphery of the columnar part 52 and extend in the axial direction.

Figure 6:
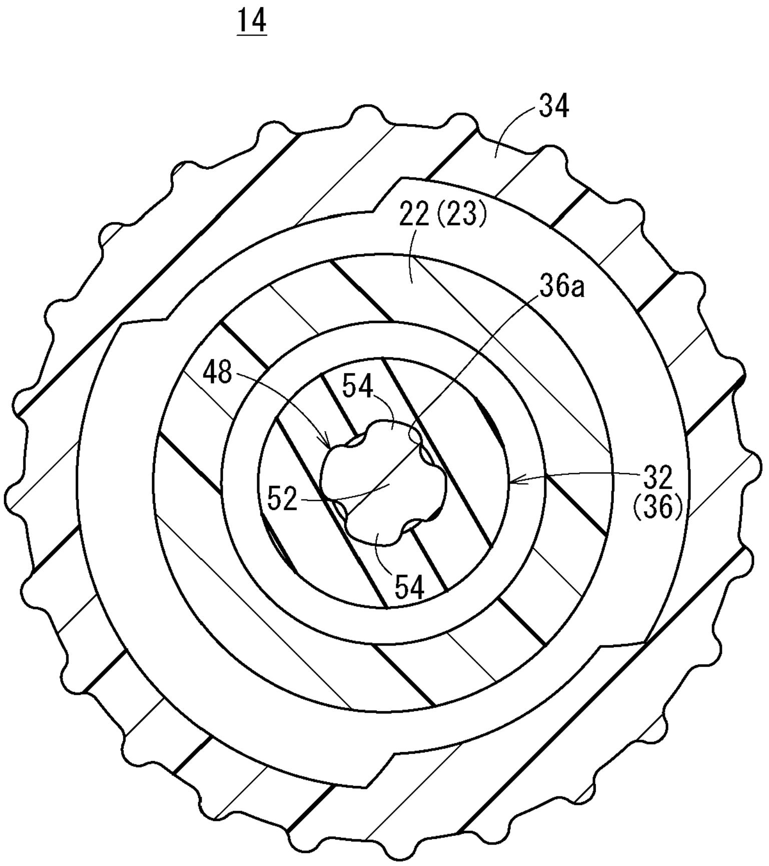
FIG. 6 is a cross-sectional view taken along the line VI-VI in FIG. 4.

The ribs 54 are provided at intervals on the outer periphery of the columnar part 52 in the circumferential direction. As shown in FIG. 6 that is a cross-sectional view taken along the line VI-VI in FIG. 4, the anti-rotation part 48 having the ribs 54 is fitted to the cylindrical part 36 in a state where the inner periphery 36*a* of the cylindrical part 36 of the elastic member 32 is elastically deformed by the anti-rotation part 48 so as to have surface irregularities. This makes it possible to prevent the relative rotation of the elastic member 32 with respect to the main body 34.

It is to be noted that the number of the ribs 54 provided on the columnar part 52 may be only one. Also in this case, the effect of preventing the relative rotation of the elastic member 32 with respect to the main body 34 can be obtained. Further, the inner periphery 36*a* of the cylindrical part 36 of the elastic member 32 may have one or more inner ribs that extend in the axial direction and radially project inward. When the number of the inner ribs is two or more, the inner ribs may be provided at intervals in the circumferential direction. In this case, the inner rib(s) of the elastic member 32 is(are) engaged with the ribs 54 of the columnar part 52, which makes it possible to further enhance the effect of preventing the relative rotation of the elastic member 32 with respect to the main body 34. The anti-rotation part 48 is not limited to one having the ribs 54, and may have any structure as long as its cross-section perpendicular to the axial direction has a non-circular profile. The anti-rotation part 48 whose cross-sectional profile is non-circular can prevent the relative rotation of the elastic member 32 with respect to the main body 34.

As shown in FIG. 4, the cover 50 extends from a base 56 of the cap 14 in the proximal direction. In a state where the cap 14 is fixed to the female luer 23, the cover 50 covers almost the entire length of the female luer 23, and the proximal end of the cover 50 is in proximity to the distal end surface 20*a* of the body part 20 of the barrel main body 12. The cover 50 is thinner and is more likely to deform as compared to the female luer 23 having the projections 30.

Figure 7:
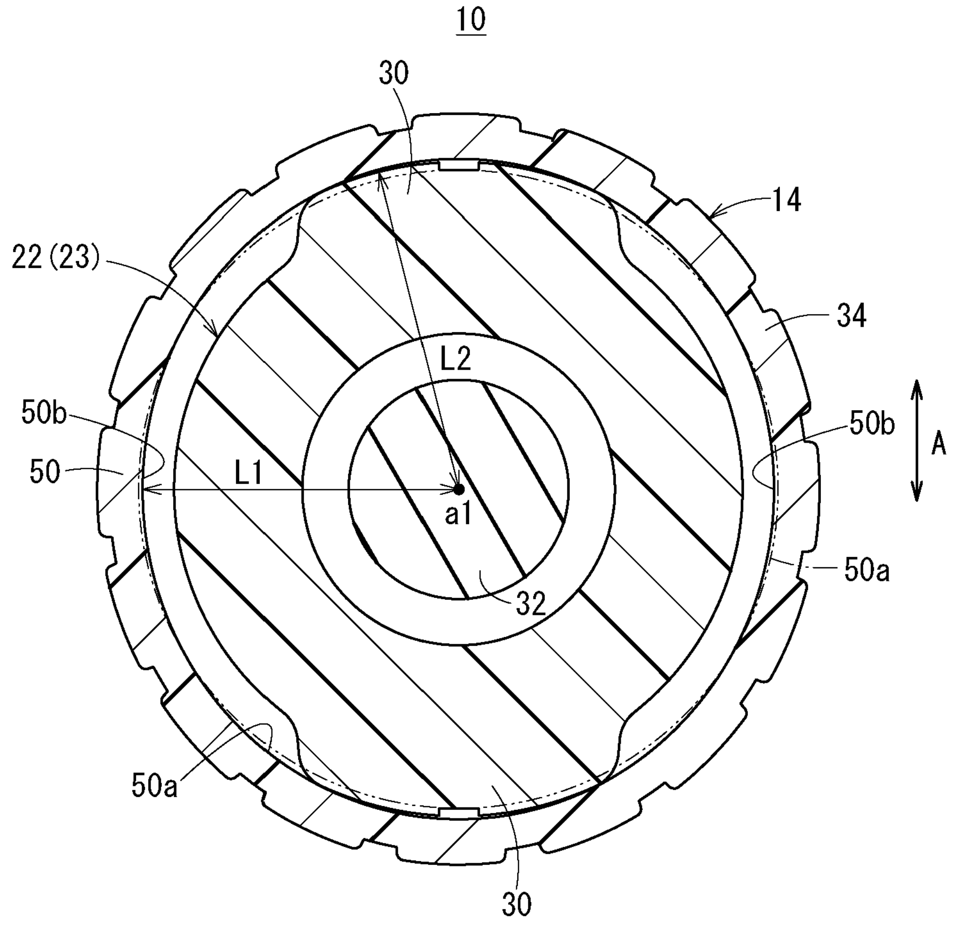
FIG. 7 is a cross-sectional view taken along the line VII-VII in FIG. 4.

As shown in FIG. 7 that is a cross-sectional view taken along the line VII-VII in FIG. 4, the proximal-side inner periphery 50*a* of the cover 50 has reduced radius portions 50*b*. A distance L1 from a rotation axis a1 of the cap 14 to each of the reduced radius portions 50*b* at the time when the cap 14 is threadedly engaged with the cylinder tip 22 is smaller than a distance L2 from the rotation axis a1 to the outer end of each of the projections 30. In this embodiment, the cross-sectional shape of the proximal-side inner periphery 50*a* of the cover 50 is not an accurate circle but an ellipse (an ellipse having a long axis in a direction represented by an arrow A in FIG. 7). Specifically, the proximal-side inner periphery 50*a* of the cover 50 is radially expanded outward by the projections 30 provided in the female luer 23, and therefore the other part of the proximal-side inner periphery 50*a* is deformed inward so that the reduced radius portions 50*b* are formed. In this embodiment, the proximal-side inner periphery 50*a* of the cover 50 has a circular cross-section perpendicular to the axis of the cover 50 before the production of the syringe barrel 18, and therefore the reduced radius portions 50*b* are provided to be opposed to each other with respect to the rotation axis a1. Therefore, the proximal-side inner periphery 50*a* of the cover 50 has an elliptical cross-sectional shape.

That is, the proximal-side inner periphery 50*a* of the cover 50 has a circular (almost true circular) cross-sectional shape represented by a chain double-dashed line in FIG. 7 at the time when the main body 34 is produced. However, when the cap 14 is attached to the barrel main body 12 in the production process of the pre-filled syringe 10, the reduced radius portions 50*b* are provided so that the proximal-side inner periphery 50*a* of the cover 50 has an elliptical cross-sectional shape. As a result, a non-circular structure formed by the proximal-side inner periphery 50*a* of the cover 50 is engaged with a non-circular structure formed by the two projections 30, and therefore the function of preventing the loosening of the cap 14 with respect to the female luer 23 delivers. Specifically, the reduced radius portions 50*b* of the cover 50 are engaged with the projections 30, and therefore the cap 14 is hard to loosen. Further, the pre-filled syringe 10 is subjected to autoclave sterilization in its production process in a state where the cap 14 is attached to the barrel main body 12. Therefore, the cap 14 is thermally deformed by high heat associated with autoclave sterilization so that the deformation of the proximal-side inner periphery 50*a* of the cover 50 by the projections 30 is established. As a result, the proximal-side inner periphery 50*a* of the cover 50 is more reliably provided with the reduced radius portions 50*b* and has an elliptical cross-sectional shape. It is to be noted that even when autoclave sterilization is not performed, deformation of the proximal-side inner periphery 50*a* of the cover 50 by the projections 30 is gradually established, and therefore the proximal-side inner periphery 50*a* of the cover 50 can be provided with the reduced radius portions 50*b* and has an elliptical cross-sectional shape.

An engagement force between the reduced radius portions 50*b* of the cover 50 and the projections 30 is larger than a disengagement force exerted on the cap 14 based on the elastic force of the elastic member 32 (specifically, the sealing part 39). This makes it possible to reliably prevent the loosening of the cap 14.

It is to be noted that the number of the projections 30 provided in the female luer 23 may be only one. Also in this case, the proximal-side inner periphery 50*a* of the cover 50 can have a non-circular cross-sectional shape to form a reduced radius portion in the production process. The projections 30 may be arranged at, for example, 60° intervals. In this case, the proximal-side inner periphery 50*a* of the cover 50 can have a cross-sectional shape close to a triangle (a triangular cross-sectional shape having round corners) to form reduced radius portions in the production process. Alternatively, the projection 30 may be formed so that its outer edge has an elliptical shape surrounding the entire outer circumference of the female luer 23. In this case, the length of the short axis of the elliptical projection 30 is smaller than the diameter of the proximal-side inner periphery 50*a* of the cover 50, and the length of the long axis of the elliptical projection 30 is larger than the diameter of the proximal-side inner periphery 50*a* of the cover 50. This makes it possible to allow the proximal-side inner periphery 50*a* of the cover 50 to have an elliptical cross-sectional shape whose short and long axes correspond to those of the elliptical shape of the projection 30 to form reduced radius portions in the production process.

Next, the gasket 16 will be described with reference to FIG. 3. The gasket 16 is inserted into the barrel main body 12. The gasket 16 has a distal end surface 60, and the distal end surface 60 has a tapered shape that becomes thinner toward the distal end. The gasket 16 has two or more ring-shaped sealing projections (in FIG. 3, two ring-shaped sealing projections) 62 formed on its outer periphery at intervals in the axial direction. In a state where the gasket 16 is inserted in the barrel main body 12, the sealing projections 62 are in close contact with the inner periphery of the barrel main body 12. Therefore, the gasket 16 is liquid-tightly and slidably movable in the barrel main body 12.

The gasket 16 may have a coating film formed on its outer surface to reduce sliding resistance against the inner periphery of the barrel main body 12. Examples of such a coating film include fluorine-based resins such as polytetrafluoroethylene (PTFE), tetrafluoroethylene.perfluoroalkylvinyl ether copolymer resin (PFA), tetrafluoroethylene.hexafluoropropylene copolymer (FEP), polychlorotrifluoroethylene (PCTFE), and polyvinylidene fluoride (PVDF), polyparaxylylene, and diamond-like carbon.

Further, in order to reduce the sliding resistance of the gasket 16 against the barrel main body 12, the inner periphery of the barrel main body 12 or the outer periphery of the gasket 16 may be coated with a liquid lubricant (e.g., silicone oil).

The gasket 16 has a fitting recess 64 provided to have an opening at its proximal end. The fitting recess 64 has a female screw 66 formed on its inner periphery. The fitting recess 64 can be threadedly engaged with the distal end of a plunger not shown. Examples of a constituent material of the gasket 16 include those mentioned above as examples of the constituent material of the elastic member 32 of the cap 14.

It is to be noted that in the pre-filled syringe 10 according to this embodiment, a gasket stopper 68 is detachably attached to the proximal end (flange 24) of the barrel main body 12 to prevent the gasket 16 from coming out of the barrel main body 12 in the proximal direction. As shown in FIG. 2 and FIG. 3, the gasket stopper 68 has a stopper plate 72 having a hole 70 that penetrates therethrough in the axial direction and has a diameter smaller than the inner diameter of the body part 20 of the barrel main body 12, and a semi-circular engagement plate 74 that is laterally opened to be engaged with the flange 24 of the barrel main body 12. The body part 20 of the barrel main body 12 is inserted into the engagement plate 74, and the flange 24 is inserted between the stopper plate 72 and the engagement plate 74 so that the gasket stopper 68 is attached to the proximal end of the barrel main body 12.

Next, the drug M will be described which is filled in the filling chamber 13 defined by the barrel main body 12, the gasket 16, and the cap 14. The drug M may be of any type, such as a powdered drug, a freeze-dried drug, a solid drug, or a liquid drug, as long as the drug M can be dissolved in or diluted with a medical liquid L (specifically, a solvent such as normal saline) filled in a dilution-side pre-filled syringe 80 (see FIG. 8B and FIG. 8C).

Examples of the drug M include protein preparations, antitumor agents, vitamin preparations (multivitamin preparations), various amino acids, antithrombotic agents such as heparin, insulin, antibiotics, pain relievers, cardiotonic agents, intravenous anesthetics, medical anesthetics, antiparkinsonian agents, anti-ulcer agents, adrenal corticosteroids, and antiarrhythmic agents.

The syringe barrel 18 and the pre-filled syringe 10 according to the present embodiment basically have such structures as described above. Hereinbelow, their functions and effects will be described.

In the production process of the pre-filled syringe 10, autoclave sterilization (high-pressure steam sterilization) is performed to achieve a predetermined cleanliness level. As one method of such sterilization, the pre-filled syringe 10 assembled as shown in FIG. 1 and FIG. 3 is subjected to sterilization. This makes it possible to sterilize the outer surface of the pre-filled syringe 10, the proximal end surface of the gasket 16 and the fitting recess 64, and the inner periphery of the barrel main body 12 located on the proximal side of the gasket 16 by exposure to high-temperature and high-pressure steam. Further, not only these areas but also the inner surface of the syringe constituting the filling chamber 13 is sterilized.

That is, since the filling chamber 13 is filled with the drug M, the inner surface of the syringe that is in contact with the drug M heated at high temperature associated with sterilization is sterilized. Further, even when a space not filled with the drug is present in the filling chamber 13, the inner surface of the syringe is sterilized with the steam of the drug M (in a case where the drug M is liquid). In this case, as shown in FIG. 4, since the annular gap 40 is created between the inner periphery 23*a* of the female luer 23 and the outer periphery of the insertion part 37 of the cap 14, the inner periphery 23*a* of the female luer 23 is effectively sterilized by the entry of the high-temperature drug M or the steam of the drug M into the gap 40.

As another method of the sterilization, the syringe barrel 18 is subjected to sterilization before the filling of the drug M and the insertion of the gasket 16. Specifically, the syringe barrel 18 is assembled by attaching the cap 14 to the barrel main body 12, and is then subjected to autoclave sterilization. In this case, since the annular gap 40 is created between the inner periphery 23*a* of the female luer 23 and the insertion part 37 of the cap 14, the inner periphery 23*a* of the female luer 23 is also effectively sterilized by the entry of high-temperature steam into the gap 40. Then, after the sterilization, the drug M is filled into the barrel main body 12 of the sterilized syringe barrel 18 in a sterilized space (e.g., in an isolator), and the gasket 16 is inserted into the barrel main body 12, and the gasket stopper 68 is finally attached. In this way, the pre-filled syringe 10 shown in FIG. 1 is completed.

The cross-sectional shape of the proximal-side inner periphery 50*a* of the cover 50 is formed by thermal deformation of the cover 50 caused by heat at the time of the above-described autoclave sterilization. That is, the cross-sectional shape of the proximal-side inner periphery 50*a* of the cover 50 before autoclave sterilization is a circle (almost true circle) as shown by a virtual line in FIG. 7. However, at the time of autoclave sterilization, the cover 50 that is thinner and is more likely to deform than the female luer 23 is softened by heat and thermally deformed in a state where the cover 50 receives a pressing force applied by the projections 30 outward in a direction represented by the arrow A. As a result, as shown in FIG. 7, the proximal-side inner periphery 50*a* of the cover 50 after sterilization has an elliptical cross-sectional shape fitted to the two projections 30 provided on the outer periphery of the female luer23. That is, irrespective to the positional relationship in the circumferential direction between the projections 30 and the cover 50, the projections 30 expand a part of the cover 50 outward, and therefore the other part of the proximal-side inner periphery 50*a* is reliably deformed inward so that the reduced radius portions 50*b* are formed. Therefore the function of preventing the loosening of the cap 14 with respect to the female luer 23 delivers.

Next, a method for operating (using) the pre-filled syringe 10 will be described mainly with reference to FIG. 3 and FIGS. 8A to 8C. As shown in FIG. 3, the pre-filled syringe 10 before use is in a state where the cap 14 is attached to the female luer 23 of the barrel main body 12. In this case, in the pre-filled syringe 10, the sealing part 39 made of an elastic material is in close contact with the distal end surface of the female luer 23 along the entire circumference of the opening 23*b*, and therefore the opening 23*b* of the female luer 23 is liquid-tightly sealed. Further, the pressing part 28 provided at the distal end of the female luer 23 presses the sealing part 39 along the entire circumference of the opening 23*b*, and therefore the pressing part 28 and the sealing part 39 are in sufficiently close contact with each other so that excellent sealing performance is achieved.

In a state where the cap 14 is attached to the female luer 23, that is, in a state where the pressing part 28 presses the sealing part 39, a force to rotate the cap 14 in a direction to loosen the cap 14 is exerted based on the elastic force of the sealing part 39. If the cap 14 is loosened before the use of the pre-filled syringe 10, there is a possibility that the leakage of the drug M occurs. For this reason, this embodiment has a structure in which the projections 30 are provided on the outer periphery of a proximal end part of the female luer 23 to prevent the loosening of the cap 14 before use. That is, the reduced radius portions 50*b* of the main body 34 (cover 50) having a non-circular shape (elliptical shape) formed by thermal deformation at the time of sterilization are engaged with the projections 30 provided on the outer periphery of a proximal end part of the female luer 23 with high accuracy. Therefore, the loosening of the cap 14 before use is effectively prevented. Specifically, when the cap 14 is tried to be rotated in a direction to loosen threaded engagement between the cap 14 and the female luer 23 in the presence of the reduced radius portions 50*b*, resistance is generated to cause the reduced radius portions 50*b* to overpass the projections 30. As a result, the cap 14 is hard to loosen. In this way, the reduced radius portions 50*b* function as a loosening-resistance generator.

Figure 8A:
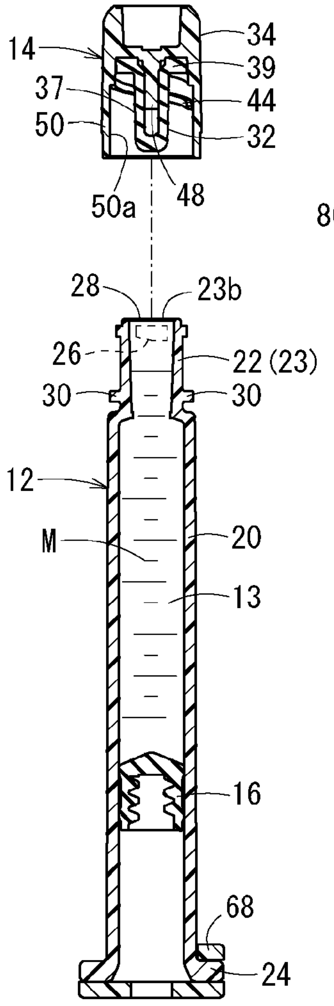
FIG. 8A is an explanatory diagram illustrating the operation of the pre-filled syringe shown in FIG. 1.

When the pre-filled syringe 10 is used, as shown in FIG. 8A, the cap 14 is opened. Specifically, the cap 14 is rotated in a predetermined direction around the barrel main body 12 to release threaded engagement between the female screw 44 and the male screw 26 to remove the cap 14 from the female luer 23. In this case, when a torque equal to or larger than a predetermined torque is applied to the cap 14, the proximal side of the main body 34 (cover 50) is elastically deformed, which allows the cap 14 to be rotated and removed.

Particularly, in this embodiment, since the projections 30 are provided on the outer periphery of a proximal end part of the female luer 23, engagement between the projections 30 and the main body 34 is released only by slightly rotating the cap 14. That is, the projections 30 and the main body 34 are engaged only in the initial stage of the operation of opening the cap 14, and thereafter, the cap 14 can be rotated with a little operating force. Therefore, the cap 14 is easily opened.

In this embodiment, since the cap 14 has the anti-rotation part 48, the elastic member 32 is rotated together with the main body 34 at the time of the operation of opening the cap 14. For this reason, the elastic member 32 is reliably separated from the pressing part 28 of the female luer 23 by rotating the cap 14. Therefore, the elastic member 32 does not remain on the female luer 23 side due to sticking to the pressing part 28 of the female luer 23.

Figure 8B:
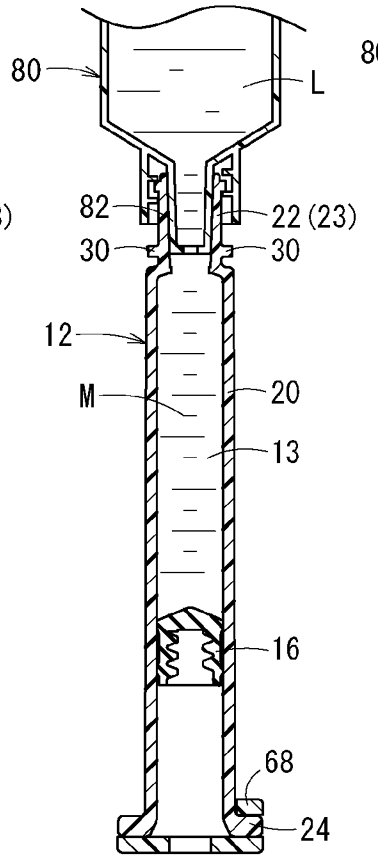
FIG. 8B is an operating explanatory diagram following FIG. 8A.

After the cap 14 is removed from the female luer 23, as shown in FIG. 8B, the pre-filled syringe 80 filled with the medical liquid L is connected to the pre-filled syringe 10. Specifically, the male luer 82 provided as a cylinder tip in the pre-filled syringe 80 is inserted into and connected to the female luer 23 of the pre-filled syringe 10. In this case, since a space corresponding to the volume of the male luer 82 is previously provided by inserting the cylindrical part 36 (insertion part 37) of the elastic member 32 into the female luer 23 in a state where the cap 14 is not opened, the drug M does not leak from the barrel main body 12 at the time when the male luer 82 is connected.

The medical liquid L filled in the pre-filled syringe 80 may be a liquid for dissolving a drug, such as distilled water for injection or normal saline, or a liquid drug that contains a drug (e.g., a vitamin preparation or a mineral) and can dissolve or dilute the drug M filled in the pre-filled syringe 10. It is to be noted that the medical liquid L is not limited to one previously filled in the pre-filled syringe 80 as in this embodiment, and may be sucked from a vial or the like into an empty syringe in a necessary amount when required.

Figure 8C:
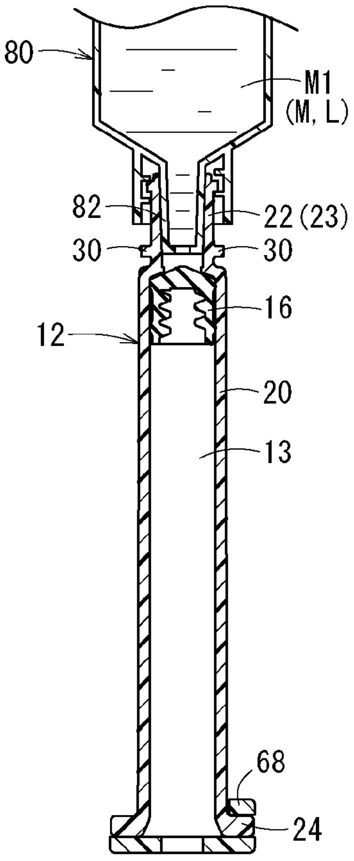
FIG. 8C is an operating explanatory diagram following FIG. 8B.

Then, as shown in FIG. 8C, a plunger (not shown) of the pre-filled syringe 80 is pulled in the proximal direction to suck the drug M from the barrel main body 12 into the pre-filled syringe 80 so that the drug M is mixed with and dissolved in or diluted with the medical liquid L in the pre-filled syringe 80. This makes it possible to prepare a desired liquid drug M1.

As has been described above, in the syringe barrel 18 and the pre-filled syringe 10 according to this embodiment, since the reduced radius portions 50*b* of the cover 50 that are engaged with the projections 30 to prevent the loosening of the cap 14 are obtained as a result of deformation caused by a force received from the projections 30, the projections 30 and the cover 50 are engaged with each other in an accurate positional relationship. Therefore, it is not necessary to align a threaded engagement structure between the cap 14 and the cylinder tip 22 with the projections 30, and therefore it is possible to easily obtain a rattle-free structure for preventing the loosening of the cap 14. Further, since the reduced radius portions 50*b* of the cover 50 that are engaged with the projections 30 are formed in the proximal-side inner periphery 50*a* of the cover 50, engagement between the projections 30 and the cover 50 is released only by slightly rotating the cap 14. Therefore, the cap 14 can be easily opened.

Further, in this embodiment, the two projections 30 are provided which project in opposite directions with respect to the axis of the cylinder tip 22. In this case, the proximal-side inner periphery 50*a* of the cover 50 is deformed by the two projections 30 provided to be opposed to each other, and has an elliptical cross-sectional shape. Therefore, the reduced radius portions 50*b* can be more reliably formed, which is highly effective at preventing the loosening of the cap 14 and makes it possible to hold the cap 14 coaxially with the cylinder tip 22.

Particularly, in this embodiment, since an engagement force between the reduced radius portions 50*b* of the cover 50 and the projections 30 is larger than a disengagement force exerted on the cap 14 based on the elastic force of the sealing part 39, the loosening of the cap 14 can be reliably prevented.

Further, since the reduced radius portions 50*b* of the cover 50 are formed by performing heat treatment in a state where the cap 14 is attached to the cylinder tip 22, a structure can be easily obtained in which the projections 30 are accurately engaged with the proximal-side inner periphery 50*a* of the cover 50. Further, since the heat treatment is autoclave sterilization performed in the production process of the syringe barrel 18 (pre-filled syringe 10), the reduced radius portions 50*b* of the cover 50 can be efficiently obtained.

Herein below, a syringe barrel 91 and a pre-filled syringe 90 according to a second embodiment of the present invention will be described with reference to FIGS. 9 to 13. It is to be noted that components of the pre-filled syringe 90 denoted by the same reference signs as those of the pre-filled syringe 10 according to the first embodiment have the same or similar functions and effects, and detailed description thereof will not be repeated.

Figure 9:
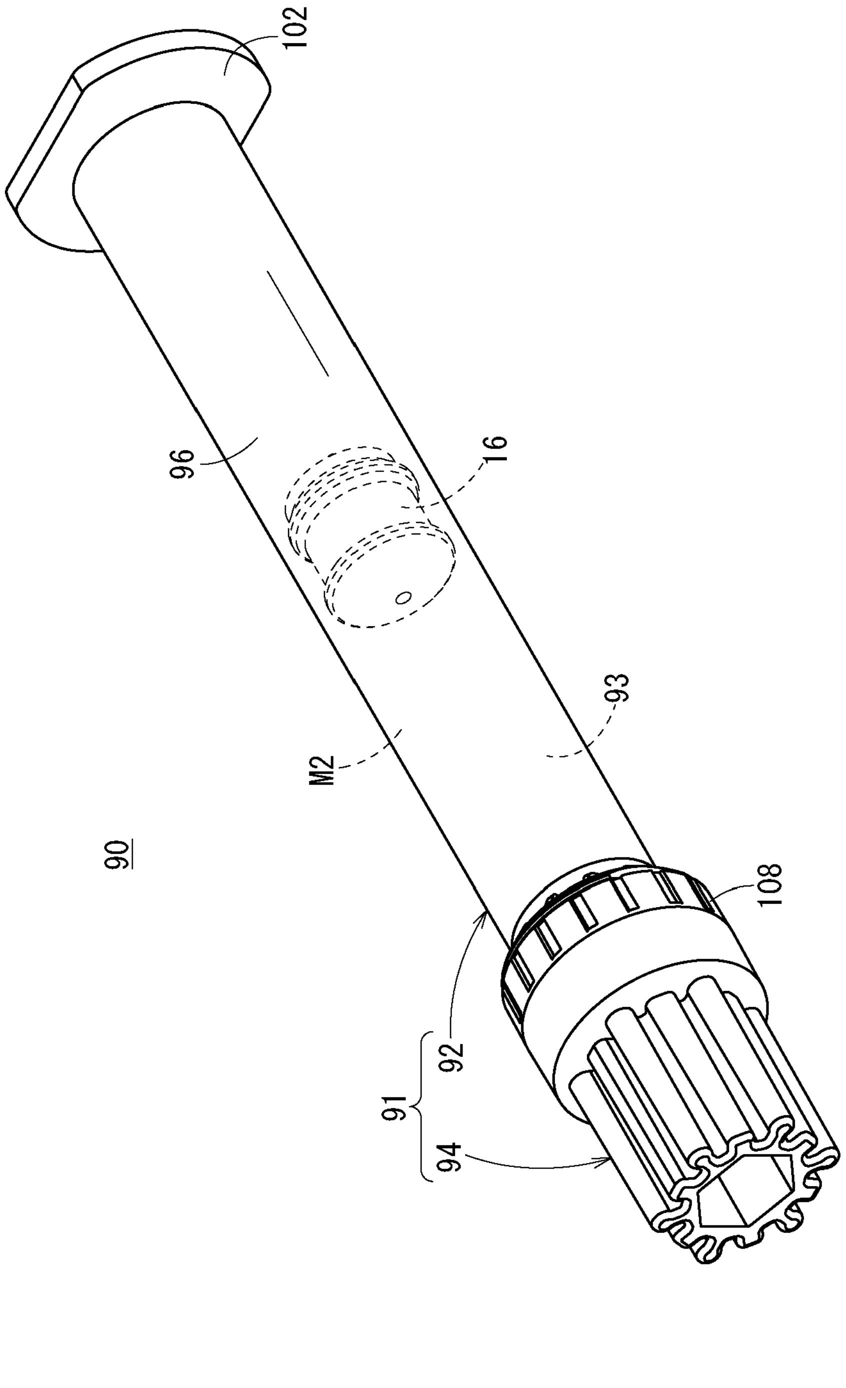
FIG. 9 is a perspective view of a pre-filled syringe according to a second embodiment of the present invention.
Figure 10:
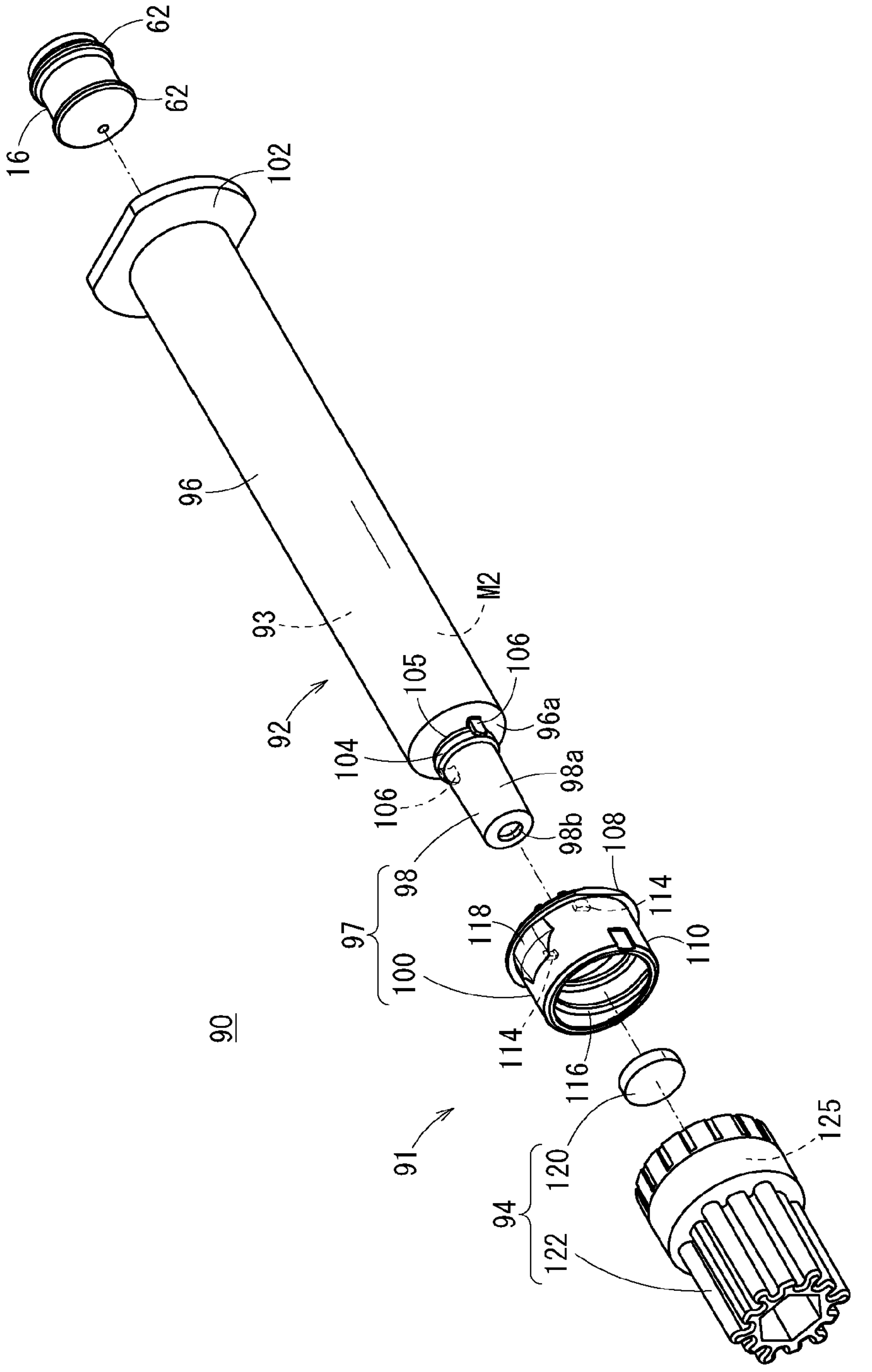
FIG. 10 is an exploded perspective view of the pre-filled syringe shown in FIG. 9.
Figure 11:
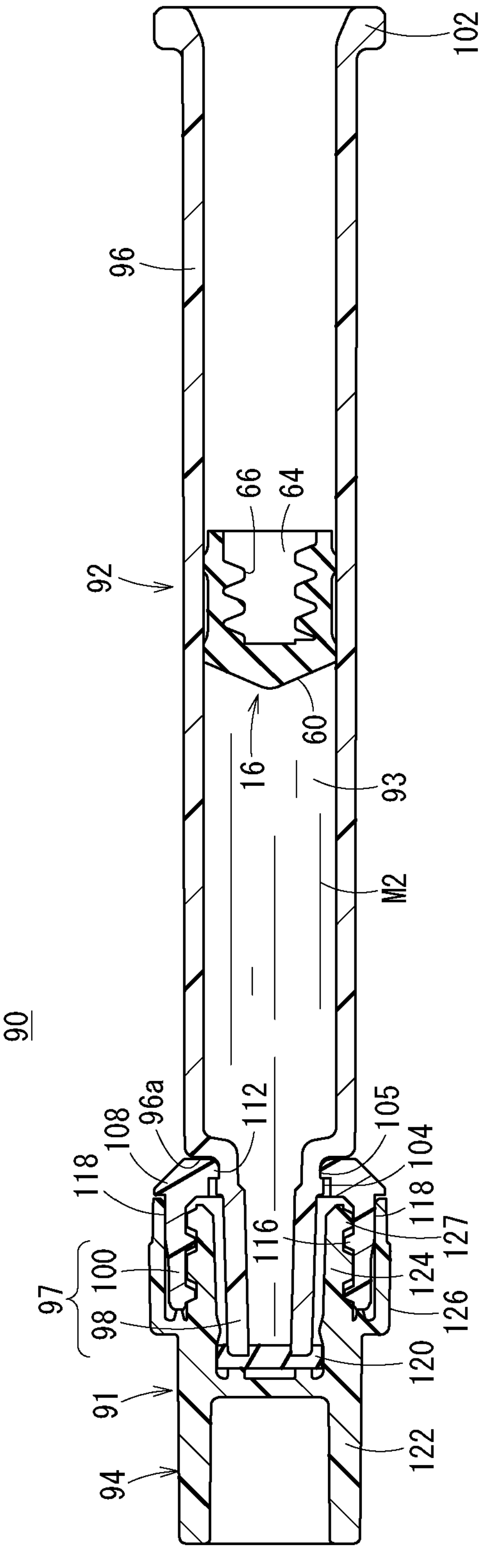
FIG. 11 is a longitudinal sectional view of the pre-filled syringe shown in FIG. 9.
Figure 12:
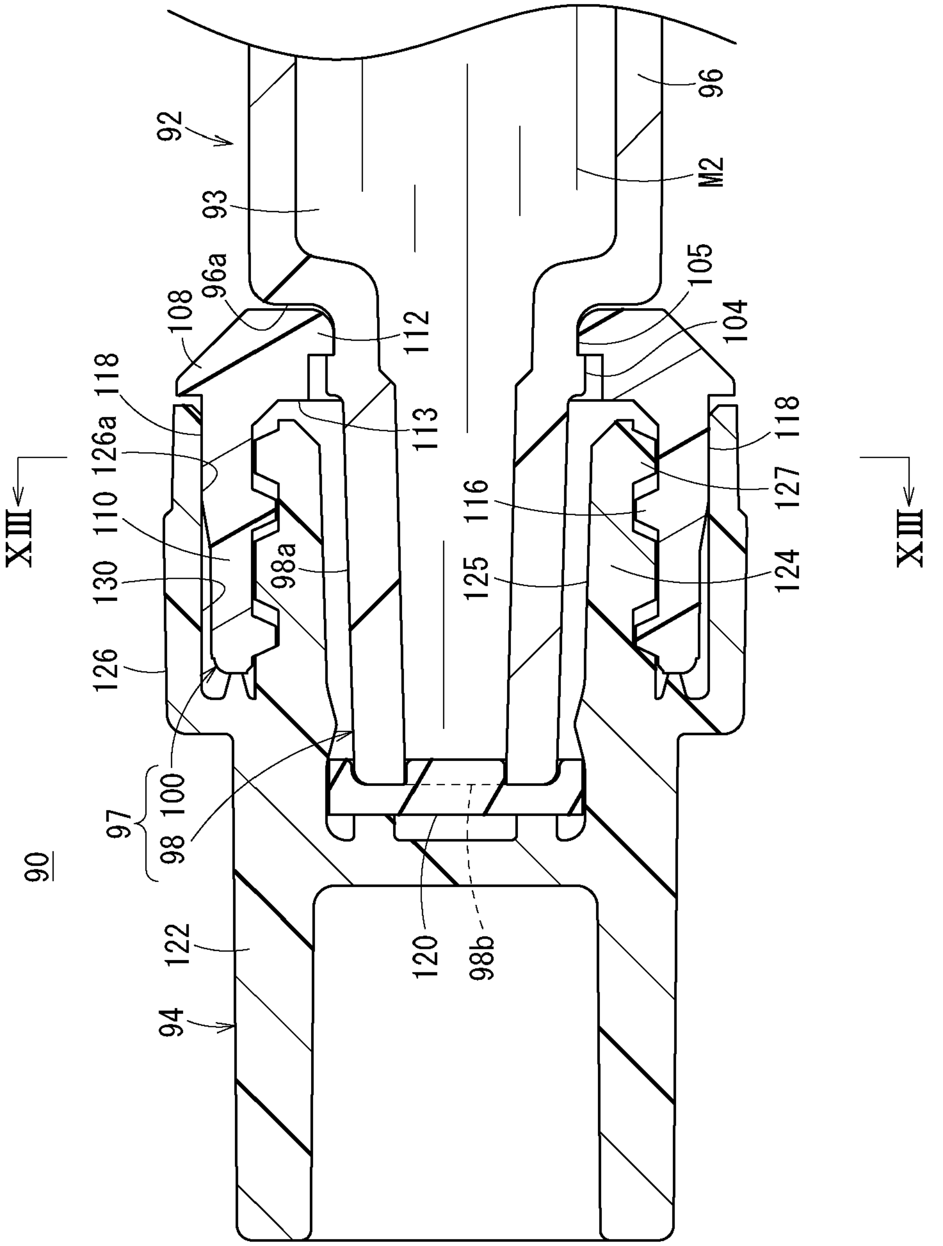
FIG. 12 is a partially-enlarged view of FIG. 11.
Figure 13:
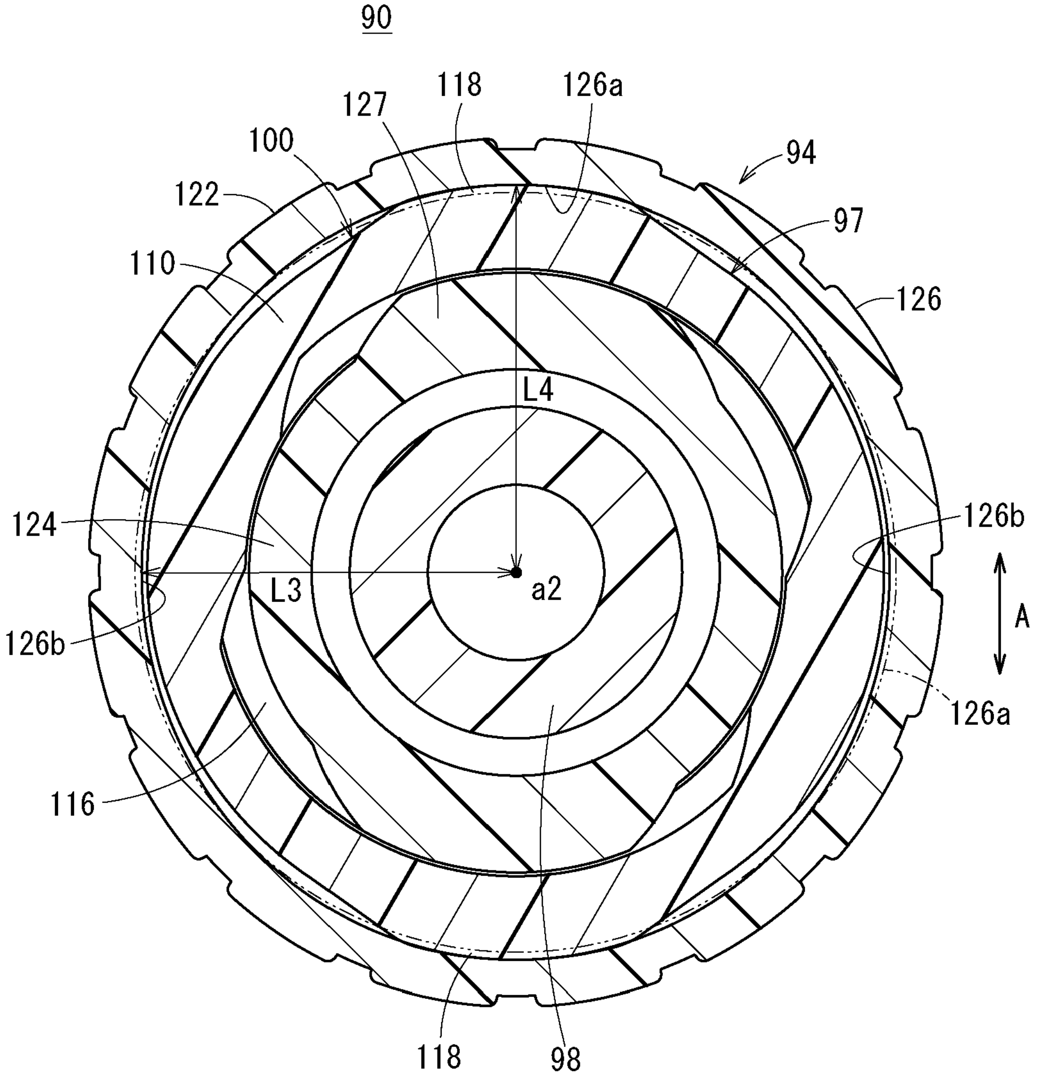
FIG. 13 is a cross-sectional view taken along the line XIII-XIII in FIG. 12.

FIG. 9 is a perspective view of a pre-filled syringe 90 according to a second embodiment of the present invention. FIG. 10 is an exploded perspective view of the pre-filled syringe 90. FIG. 11 is a longitudinal sectional view of the pre-filled syringe 90. FIG. 12 is an enlarged longitudinal sectional view of the distal end of the pre-filled syringe 90. FIG. 13 is a cross-sectional view taken along the line XIII-XIII in FIG. 12.

The pre-filled syringe 90 includes, as its main components, a cylindrical barrel main body 92 having a cylinder tip 97, a cap 94 that seals the cylinder tip 97 of the barrel main body 92, a gasket 16 that is liquid-tightly and slidably movable in the barrel main body 92, and a drug M2 filled in a filling chamber 93 formed in the barrel main body 92. In this pre-filled syringe 90, the barrel main body 92 and the cap 94 constitute a syringe barrel 91.

As shown in FIG. 10 and FIG. 11, the barrel main body 92 has a body part 96 constituting the main part of the barrel main body 92, a male luer 98 provided at the distal end of the body part 96, a lock adaptor 100 placed outside the male luer 98, and a flange 102 formed to radially project outward from the proximal end of the body part 96. The body part 96, the male luer 98, and the flange 102 are integrally formed. In the pre-filled syringe 90, the cylinder tip 97 is constituted from the male luer 98 and the lock adaptor 100.

The male luer 98 can be inserted and connected to a female luer not shown, and projects from the distal end of the barrel main body 92 in the distal direction so as to have a diameter smaller than that of the barrel main body 92. The male luer 98 has a tapered outer periphery 98*a* whose outer diameter decreases toward the distal direction. An annular outward engagement projection 104 that projects outward is provided on the outer periphery of a proximal end part of the male luer 98, and an annular engagement recess 105 is formed between the outward engagement projection 104 and a distal end surface 96*a* of the body part 96. Further, two or more ribs 106 (in FIG. 10, two ribs 106) are provided on the outer periphery of a proximal end part of the male luer 98 at intervals in the circumferential direction.

As shown in FIG. 12, the lock adaptor 100 is a hollow member placed outside the male luer 98 so as to surround the male luer 98. The lock adaptor 100 has a base 108 connected to the proximal end of the male luer 98 and a cylindrical wall 110 that extends from the base 108 in the distal direction.

An annular inward engagement projection 112 that projects inward is provided on the inner periphery of the base 108. The inward engagement projection 112 has an inner end, and the inner end is placed in the engagement recess 105 and engaged with the outward engagement projection 104 to prevent the lock adaptor 100 from being pulled out in the distal direction. Further, as shown in FIG. 10, a plurality of (two) slots 114 are provided in the proximal-side inner periphery of the base 108 at intervals in the circumferential direction so as to be engaged with the ribs 106. The engagement between the ribs 106 and the slots 114 prevents the relative rotation of the lock adaptor 100 with respect to the male luer 98.

The cylindrical wall 110 is an almost hollow cylindrical part that extends in the axial direction so as to surround the male luer 98 so that an annular recess 113 that is opened in the distal direction is formed between the cylindrical wall 110 and the male luer 98 (see FIG. 12). In the inner periphery of the cylindrical wall 110, a female screw 116 is formed to detachably fix the cap 94.

On the proximal-side outer periphery of the cylindrical wall 110, a projection 118 is provided to prevent the loosening of the cap 94 before use. In this embodiment, a pair of projections 118 is provided which projects in opposite directions with respect to the axis of the barrel main body 92. In a state where the cap 94 is fixed to the cylinder tip 97, the projections 118 are engaged with a proximal-side inner periphery 126*a* of a cover 126 that will be described later. In this way, the projections 118 prevent the loosening of threaded engagement between the cap 94 and the cylinder tip 97. It is to be noted that the function of the projection 118 to prevent the loosening of the cap 94 will be described again after description of the specific structure of the cap 94.

It is to be noted that the lock adaptor 100 shown in the drawings is provided as a part separated from the male luer 98 and the body part 96, but may be integrally provided with the proximal end of the male luer 98 or the distal end of the body part 96.

Examples of a constituent material of the barrel main body 92 having such a structure as described above include various resins such as polypropylene, polyethylene, polystyrene, polyamide, polycarbonate, polyvinyl chloride, poly-(4-methylpentene-1), acrylic resins, acrylonitrile-butadiene-styrene copolymers, polyesters such as polyethylene terephthalate, and cyclic polyolefins. Among them, resins such as polypropylene and cyclic polyolefins are preferred for ease of molding and heat resistance.

Next, the structure of the cap 94 detachably attached to the cylinder tip 97 will be described. As shown in FIGS. 10 to 12, the cap 94 has a sealing part 120 that seals an opening 98*b* of the male luer 98 and a main body 122 that supports the sealing part 120. In a state where the cap 94 is attached to the cylinder tip 97 before use, the opening 98*b* of the male luer 98 is liquid-tightly sealed with the cap 94 (see FIG. 10) so that the drug M2 does not leak through the opening 98*b*.

The sealing part 120 is made of an elastic material and is placed in the main body 122 (in a recess 125 that will be described later). The sealing part 120 shown in the drawings is formed into a disc shape having a diameter larger than that of the opening 98*b* of the male luer 98.

Examples of a constituent material of the sealing part 120 include: various rubber materials such as natural rubber, butyl rubber, isoprene rubber, butadiene rubber, styrene-butadiene rubber, and silicone rubber; various thermoplastic elastomers such as polyurethane-based thermoplastic elastomers, polyester-based thermoplastic elastomers, polyamide-based thermoplastic elastomers, olefin-based thermoplastic elastomers, and styrene-based thermoplastic elastomers; and mixtures of two or more of them.

In a state where the cap 94 is fixed (attached) to the cylinder tip 97, the sealing part 120 is in close contact with the distal end surface of the male luer 98 along the entire circumference of the opening 98*b* of the male luer 98, and is dented in the distal direction by pressing with the distal end surface in the distal direction. It is to be noted that the sealing part 120 has a flat proximal end surface in its natural state (in a state where the sealing part 120 is not pressed with the distal end surface of the male luer 98).

The main body 122 of the cap 94 is made of a material harder than the sealing part 120 (e.g., a material mentioned above as an example of the constituent material of the barrel main body 92). The main body 122 has a hollow housing 124 in which the male luer 98 is housed in a state where the cap 94 is attached to the cylinder tip 97, and a cover 126 provided outside the housing 124.

The housing 124 has an almost cylindrical recess 125 that has a closed distal end and an open proximal end. The sealing part 120 is placed and held at the bottom of the recess 125. The inner diameter of the housing 124 is larger than the outer diameter of the male luer 98. Therefore, in a state where the cap 94 is attached to the cylinder tip 97, the inner periphery of the housing 124 and the outer periphery 98*a* of the male luer 98 are not in contact with each other, and a tubular gap is created between the inner periphery and the outer periphery 98*a*. Further, the outer periphery of the housing 124 has a male screw 127 that is threadedly engaged with the female screw 116 of the cylinder tip 97.

The cover 126 is a hollow cylindrical part formed to be concentric with the housing 124. Between the cover 126 and the housing 124, an annular insertion recess 130 opened in the proximal direction is formed. The lock adaptor 100 is inserted into the insertion recess 130. The cover 126 is thinner and is more likely to deform than the lock adaptor 100 having the projections 118. In a state where the cap 94 is attached to the cylinder tip 97, the cover 126 covers (the cylindrical wall 110 of) the lock adaptor 100 of the cylinder tip 97, and is engaged with the projections 118 of the lock adaptor 100.

As shown in FIG. 13, the proximal-side inner periphery 126*a* of the cover 126 has reduced radius portions 126*b*. A distance L3 from a rotation axis a2 of the cap 94 to each of the reduced radius portions 126*b* at the time when the cap 94 is threadedly engaged with the cylinder tip 97 (lock adaptor 100) is smaller than a distance L4 from the rotation axis a2 to the outer end of each of the projections 118. In this embodiment, the cross-sectional shape of the proximal-side inner periphery 126*a* of the cover 126 is not an accurate circle but an ellipse (an ellipse having a long axis in a direction represented by an arrow A in FIG. 13). Specifically, the proximal-side inner periphery 126*a* of the cover 126 is radially expanded outward by the projections 118, and therefore the other part of the proximal-side inner periphery 126*a* is deformed inward so that the reduced radius portions 126*b* are formed. In this embodiment, the proximal-side inner periphery 126*a* of the cover 126 has a circular cross-section perpendicular to the axis of the cover 126 before the production of the syringe barrel 91, and therefore the reduced radius portions 126*b* are provided to be opposed to each other with respect to the rotation axis a2. Therefore, the proximal-side inner periphery 126*a* of the cover 126 has an elliptical cross-sectional shape.

That is, the proximal-side inner periphery 126*a* of the cover 126 has a circular (almost true circular) cross-sectional shape represented by a chain double-dashed line in FIG. 13 at the time when the main body 122 is produced. However, when the cap 94 is attached to the barrel main body 92 in the production process of the pre-filled syringe 90, the reduced radius portions 126*b* are provided so that the proximal-side inner periphery 126*a* of the cover 126 has an elliptical cross-sectional shape. As a result, a non-circular structure formed by the proximal-side inner periphery 126*a* of the cover 126 is engaged with a non-circular structure formed by the two projections 118, and therefore the function of preventing the loosening of the cap 94 with respect to the cylinder tip 97 delivers. Specifically, the reduced radius portions 126*b* of the cover 126 are engaged with the projections 118, and therefore the cap 94 is hard to loosen. Further, the pre-filled syringe 90 is subjected to autoclave sterilization in its production process in a state where the cap 94 is attached to the barrel main body 92. Therefore, the cap 94 is thermally deformed by high heat associated with autoclave sterilization so that the deformation of the proximal-side inner periphery 126*a* of the cover 126 by the projections 118 is established. As a result, the proximal-side inner periphery 126*a* of the cover 126 is more reliably provided with the reduced radius portions 126*b* and has an elliptical cross-sectional shape. It is to be noted that even when autoclave sterilization is not performed, deformation of the proximal-side inner periphery 126*a* of the cover 126 by the projections 118 is gradually established, and therefore the proximal-side inner periphery 126*a* of the cover 126 can be provided with the reduced radius portions 126*b* and has an elliptical cross-sectional shape.

An engagement force between the cover 126 and the projections 118 is larger than a disengagement force exerted on the cap 94 based on the elastic force of the sealing part 120. In a state where the cap 94 is fixed to the cylinder tip 97, the proximal-side inner periphery 126*a* of the cover 126 is engaged with the projections 118 provided in the lock adaptor 100, which prevents the loosening of the cap 94.

It is to be noted that the number of the projections 118 provided in the lock adaptor 100 may be only one. Also in this case, the proximal-side inner periphery 126*a* of the cover 126 can have a non-circular cross-sectional shape to form a reduced radius portion in the production process. The projections 118 may be arranged at, for example, 60° intervals. In this case, the proximal-side inner periphery 126*a* of the cover 126 can have a cross-sectional shape close to a triangle (a triangular cross-sectional shape having round corners) to form reduced radius portions in the production process. Alternatively, the projection 118 may be formed so that its outer edge has an elliptical shape surrounding the entire outer circumference of the lock adaptor 100. In this case, the length of the short axis of the elliptical projection 118 is smaller than the diameter of the proximal-side inner periphery 126*a* of the cover 126, and the length of the long axis of the elliptical projection 118 is larger than the diameter of the proximal-side inner periphery 126*a* of the cover 126. This makes it possible to allow the proximal-side inner periphery 126*a* of the cover 126 to have an elliptical cross-sectional shape whose short and long axes correspond to those of the elliptical shape of the projection 118 to form reduced radius portions in the production process.

The gasket 16 of the pre-filled syringe 90 has the same structure as the gasket 16 of the pre-filled syringe 10 according to the first embodiment. Examples of the drug M2 filled in the filling chamber 93 include: various liquid drugs such as injections for correcting electrolyte imbalance (e.g., sodium chlorite, potassium lactate), vitamin preparations, vaccines, antibiotic injections, steroids, insulin, antibody drugs, proteolytic enzyme inhibitors, fat emulsions, various protein preparations, anticancer drugs, anesthetics, stimulants, and narcotics; and various diagnostic agents.

The syringe barrel 91 and the pre-filled syringe 90 according to the present embodiment basically have such structures as described above. Hereinbelow, their functions and effects will be described.

In the production process of the pre-filled syringe 90, autoclave sterilization (high-pressure steam sterilization) is performed to achieve a predetermined cleanliness level. The cross-sectional shape of the proximal-side inner periphery 126*a* of the cover 126 is formed by thermal deformation of the cover 126 caused by heat at the time of autoclave sterilization. That is, the cross-sectional shape of the proximal-side inner periphery 126*a* of the cover 126 before autoclave sterilization is a circle (almost true circle) as shown by a virtual line in FIG. 13. However, at the time of autoclave sterilization, the cover 126 that is thinner and is more likely to deform than the lock adaptor 100 is softened by heat and thermally deformed in a state where the cover 126 receives a pressing force applied by the projections 118 outward in a direction represented by the arrow A. As a result, as shown in FIG. 13, the proximal-side inner periphery 126*a* of the cover 126 after sterilization has an elliptical cross-sectional shape fitted to the two projections 118. That is, irrespective to the positional relationship in the circumferential direction between the projections 118 and the cover 126, the projections 118 expand a part of the cover 126 outward, and therefore the other part of the proximal-side inner periphery 126*a* is reliably deformed inward so that the reduced radius portions 126*b* are formed. Therefore the function of preventing the loosening of the cap 94 with respect to the cylinder tip 97 delivers.

A method for operating (using) the pre-filled syringe 90 will be roughly described below. As shown in FIG. 11, the pre-filled syringe 90 before use is in a state where the cap 94 is attached to the cylinder tip 97 of the barrel main body 92. In this case, in the pre-filled syringe 90, the sealing part 120 made of an elastic material is in close contact with the distal end surface of the male luer 98 along the entire circumference of the opening 98*b*, and the distal end surface of the male luer 98 presses the sealing part 120 in the distal direction. Therefore, the opening 98*b* of the male luer 98 is liquid-tightly sealed.

In such a state where the cap 94 is attached to the cylinder tip 97, that is, in a state where the pressing part 28 presses the sealing part 120, a force to rotate the cap 94 in a direction to loosen the cap 94 is exerted based on the elastic force of the sealing part 120. If the cap 94 is loosened before the use of the pre-filled syringe 90, there is a possibility that the leakage of the drug M2 occurs. For this reason, this embodiment has a structure in which the projections 118 are provided on the proximal-side outer periphery of the lock adaptor 100 to prevent the loosening of the cap 94 before use. That is, the reduced radius portions 126*b* of the main body 122 (cover 126) having a non-circular shape (elliptical shape) formed by thermal deformation at the time of sterilization are engaged with the projections 118 provided on the proximal-side outer periphery of the lock adaptor 100 with high accuracy. Therefore, the loosening of the cap 94 before use is effectively prevented. Specifically, when the cap 94 is tried to be rotated in a direction to loosen threaded engagement between the cap 94 and the lock adaptor 100 in the presence of the reduced radius portions 126*b*, resistance is generated to cause the reduced radius portions 126*b* to overpass the projections 118. As a result, the cap 94 is hard to loosen. In this way, the reduced radius portions 126*b* function as a loosening-resistance generator.

When the pre-filled syringe 90 is used, the cap 94 is opened. Specifically, the cap 94 is rotated in a predetermined direction around the barrel main body 92 to release threaded engagement between the female screw 116 and the male screw 127 to remove the cap 94 from the cylinder tip 97. In this case, when a torque equal to or larger than a predetermined torque is applied to the cap 94, the proximal side of the main body 122 (cover 126) is elastically deformed, which allows the cap 94 to be rotated and removed.

Particularly, in this embodiment, since the projections 118 are provided on the proximal-side outer periphery of the lock adaptor 100, engagement between the projections 118 and the main body 122 is released only by slightly rotating the cap 94. That is, the projections 118 and the main body 122 are engaged only in the initial stage of the operation of opening the cap 94, and thereafter, the cap 94 can be rotated with a little operating force. Therefore, the cap 94 is easily opened.

In a case where a plunger is not previously connected to the gasket 16, a plunger is connected to the gasket 16, and then the cap 94 is opened. After the cap 94 is removed from the cylinder tip 97, the male luer 98 is connected to a transfusion line or the like not shown, and the drug M2 is administered by operating the plunger. It is to be noted that a plunger may be previously connected to the gasket 16 of the pre-filled syringe 90.

As has been described above, in the syringe barrel 91 and the pre-filled syringe 90 according to this embodiment, since the reduced radius portions 126*b* of the cover 126 that are engaged with the projections 118 to prevent the loosening of the cap 94 are obtained as a result of deformation caused by a force received from the projections 118, the projections 118 and the cover 126 are engaged with each other in an accurate positional relationship. Therefore, it is not necessary to align a threaded engagement structure between the cap 94 and the cylinder tip 97 with the projections 118, and therefore it is possible to easily obtain a rattle-free structure for preventing the loosening of the cap 94. Further, since the reduced radius portions 126*b* of the cover 126 that are engaged with the projections 118 are formed in the proximal-side inner periphery 126*a* of the cover 126, engagement between the projections 118 and the cover 126 is released only by slightly rotating the cap 94. Therefore, the cap 94 can be easily opened.

Further, in this embodiment, the two projections 118 are provided which project in opposite directions with respect to the axis of the cylinder tip 97. In this case, the proximal-side inner periphery 126*a* of the cover 126 is deformed by the two projections 118 provided to be opposed to each other, and has an elliptical cross-sectional shape. Therefore, the reduced radius portions 126*b* can be more reliably formed, which is highly effective at preventing the loosening of the cap 94 and makes it possible to hold the cap 94 coaxially with the cylinder tip 97.

Particularly, in this embodiment, since an engagement force between the reduced radius portions 126*b* of the cover 126 and the projections 118 is larger than a disengagement force exerted on the cap 94 based on the elastic force of the sealing part 120, the loosening of the cap 94 can be reliably prevented.

Further, since the reduced radius portions 126*b* of the cover 126 are formed by performing heat treatment in a state where the cap 94 is attached to the cylinder tip 97, a structure can be easily obtained in which the projections 118 are accurately engaged with the proximal-side inner periphery 126*a* of the cover 126. Further, since the heat treatment is autoclave sterilization performed in the production process of the pre-filled syringe 90, the reduced radius portions 126*b* of the cover 126 can be efficiently obtained.

Embodiments of the present invention have been described above, but the present invention is not limited to the above-described embodiments. Various changes may be made without departing from the scope of the present invention.

The invention claimed is:

1. A syringe barrel comprising:

an barrel main body having a cylinder tip at a distal end of the barrel main body; and a cap detachably attached to the cylinder tip by threaded engagement to seal an opening of the cylinder tip, wherein the cylinder tip comprises at least one projection that projects radially from an outer periphery of a proximal end part of the cylinder tip, wherein the cap includes a cylindrical cover that covers an outer periphery of the cylinder tip, wherein a proximal-side inner periphery of the cover comprises a reduced radius portion, and, when the cap is threadedly engaged with the cylinder tip, a distance from a rotation axis of the cap to the reduced radius portion is smaller than a distance from the rotation axis to an outer end of the at least one projection, wherein a portion of the proximal-side inner periphery of the cover is expanded outwardly by the at least one projection, which deforms another portion of the proximal-side inner periphery inwardly, thereby forming the reduced radius portion, and wherein the reduced radius portion is engaged with the at least one projection to prevent loosening of the cap when the cap is attached to the cylinder tip.

2. The syringe barrel according to claim 1, wherein, before the cap is engaged with the cylinder tip, the proximal-side inner periphery of the cover has a circular cross-sectional shape in a plane perpendicular to an axis of the cover.

3. The syringe barrel according to claim 2, wherein the at least one projection comprises two projections that project in opposite directions from an axis of the cylinder tip.

4. The syringe barrel according to claim 1, wherein:

the cap includes a sealing part that is in contact with a distal end of the cylinder tip and is made of an elastic material, and when the cap is attached to the cylinder tip, the sealing part is pressed by the distal end of the cylinder tip to seal the opening of the cylinder tip.

5. The syringe barrel according to claim 4, wherein an engagement force between the reduced radius portion of the cover and the projection is larger than a disengagement force exerted on the cap based on an elastic force of the sealing part.

6. The syringe barrel according to claim 1, wherein the reduced radius portion of the cover is formed by performing heat treatment in a state in which the cap is attached to the cylinder tip.

7. The syringe barrel according to claim 6, wherein the heat treatment is autoclave sterilization.

8. The syringe barrel according to claim 1, wherein the cylinder tip comprises a female luer configured such that a male luer is insertable into and connectable to the female luer.

9. The syringe barrel according to claim 1, wherein:

the cylinder tip comprises:

a male luer that is insertable into and connectable to a female luer, and a cylindrical lock adaptor surrounding an outer periphery of the male luer and having a female screw formed on a inner periphery of the cylindrical lock adapter, and the at least one projection is formed on an outer periphery of the lock adaptor.

10. A pre-filled syringe comprising:

the syringe barrel according to claim 1;

a gasket that is slidably movable in the barrel main body in a liquid-tight manner; and a drug filled in a filling chamber defined by the barrel main body, the gasket, and the cap.

* * * * *